(12) United States Patent  (10) Patent No.: US 6,699,876 B2
Lavielle et al.  (45) Date of Patent: Mar. 2, 2004

(54) CAMPTOTHECIN ANALOGUE COMPOUNDS

(75) Inventors: Gilbert Lavielle, La celle Saint Cloud (FR); Patrick Hautefaye, Servon Brie Comte Robert (FR); Alain Pierre, Les Alluets le Roi (FR); Ghanem Atassi, Saint Cloud (FR); John Hickman, Puteaux (FR); Bernard Cimetiere, Paris (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/300,330

(22) Filed: Nov. 20, 2002

(65) Prior Publication Data

US 2003/0105109 A1 Jun. 5, 2003

Related U.S. Application Data

(63) Continuation-in-part of application No. 10/010,380, filed on Nov. 5, 2001, now Pat. No. 6,509,345, which is a continuation of application No. 09/715,230, filed on Nov. 17, 2000, now abandoned.

(30) Foreign Application Priority Data

Nov. 18, 1999 (FR) ............................... 99 14499

(51) Int. Cl.⁷ ..................... A61K 31/4375; A61P 35/00; C07D 471/14
(52) U.S. Cl. ........................... 514/283; 546/36; 546/41; 546/51
(58) Field of Search .................... 514/283; 546/36, 546/41, 51

(56) References Cited

U.S. PATENT DOCUMENTS 6,043,367 A * 3/2000 Roffler et al. ............... 546/48

FOREIGN PATENT DOCUMENTS

DE 198 15 812 * 10/1999

OTHER PUBLICATIONS

Rigby et al. (Tetrahedron Letters, vol. 38, No. 28, pp. 4969–4972) 1997.*

* cited by examiner

*Primary Examiner*—Bruck Kifle
(74) *Attorney, Agent, or Firm*—The Firm of Hueschen and Sage

(57) ABSTRACT

Compound of formula (I):

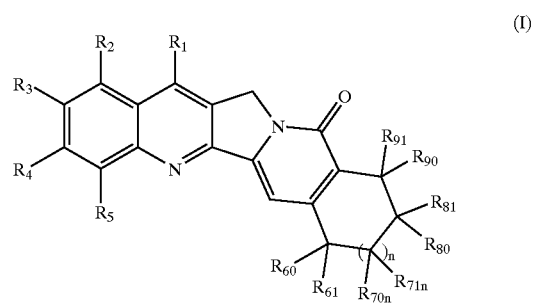

wherein:

n is 0, 1 or 2, $R_1$ represents $(C_3–C_{11})$cycloalkyl or $(C_3–C_{11})$cycloalkylalkyl, $R_2$, $R_3$, $R_4$ and $R_5$ are selected from hydrogen, halogen, alkyl, alkenyl, alkynyl, perhaloalkyl, cycloalkyl, cycloalkylalkyl, hydroxy, hydroxyalkyl, alkoxy, alkoxyalkyl, alkoxycarbonyl, acyloxy, carboxy, nitro, cyano, aminocarbonyl (optionally substituted), and the groups $(CH_2)_p$—$N_aR_b$ and —O—C(O)—N—$R_aR_b$, with p, $R_a$ and $R_b$ being as defined in the description, or two adjacent groups $R_2$, $R_3$, $R_4$ and $R_5$ together form a group —O—$(CH_2)_t$—O, t being integer from 1 to 3, $R_{60}$, $R_{70n}$, $R_{80}$ and $R_{90}$ represent a hydrogen atom, a hydroxy group, an alkoxy group, or an O—(CO)—X or O—(CO)—NXW group as defined in the description, $R_{61}$, $R_{71n}$, $R_{81}$, and $R_{91}$ represent a hydrogen atom, alkyl, alkenyl or alkynyl, or taken in pairs together form a bond or an oxirane group, or two groups together form an oxo group.

and medicinal products containing the same are useful for the treatment of cancerous disesases.

6 Claims, No Drawings

CAMPTOTHECIN ANALOGUE COMPOUNDS

The present invention relates to new camptothecin analogue compounds.

DESCRIPTION OF THE PRIOR ART

Camptothecin, an alkaloid isolated from *Camptotheca accuminata*, is an anti-cancer agent having a broad spectrum of activity. Its insoluble nature has for a long time directed research towards the insoluble salts of the compound, the toxicity of which has proved to be a major handicap. Several other studies have been carried out with a view to obtaining structural analogues and to overcoming the lack of solubility of the natural molecule (J. Med. Chem., 1991, 34, 98; Chem. Pharm. Bull., 1991, 39, 3183). The modifications made relate principally to the A and B rings. The conclusions of different studies also show the importance of the E ring and more especially of the lactone function. In fact, the latter, in equilibrium with the open hydroxy-acid form, appears to be the most active form having reduced undesirable effects (Cancer Res., 1989, 49, 1465; ibid, 1989, 49, 5077). Attempts at modifying this ring have been carried out, in particular the cyclic oxygen atom has been replaced by a nitrogen or sulphur atom, but in each case there is a loss of pharmacological activity, so confirming the importance of the lactone (J. Med. Chem., 1989, 32, 715).

BACKGROUND OF THE INVENTION

The present invention relates to camptothecin structural analogue compounds, the E ring of which has been modified. They are characterised by the replacement of the lactone function of that ring by a cyclic ketone function, the cyclic oxygen having been replaced by a carbon atom. The compounds so obtained have a novel structure and, surprisingly, have a significant cytotoxic character. It will therefore be possible to use them in the manufacture of medicaments for use in the treatment of cancerous diseases.

DETAILED DESCRIPTION OF THE INVENTION

The invention relates to the compounds of formula (I):

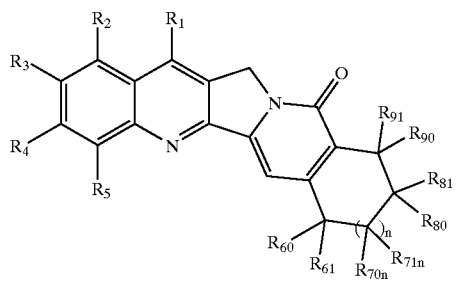

(I)

wherein:

n is 0, 1 or 2, $R_1$ represents $(C_3–C_{11})$cycloalkyl or $(C_3–C_{11})$ cycloalkylalkyl, $R_2$, $R_3$, $R_4$ and $R_5$ are selected each independently of the others from a hydrogen atom, a halogen atom, an alkyl group, an alkenyl group, an alkynyl group, a perhaloalkyl group, a $(C_3–C_{11})$cycloalkyl group, a $(C_3–C_{11})$ cycloalkyl-alkyl group, a hydroxy group, a hydroxyalkyl group, an alkoxy group, an alkoxyalkyl group, an alkoxycarbonyl group, an acyloxy group, a carboxy group, a nitro group, a cyano group, an aminocarbonyl group (optionally substituted on the nitrogen atom by one or two alkyl groups), and the groups $(CH_2)_p$—$NR_aR_b$ and —O—C(O)—N—$R_aR_b$, wherein p is an integer from 0 to 6, and $R_a$ and $R_b$ each independently of the other represents a hydrogen atom, an alkyl group, a $(C_3–C_{11})$cycloalkyl group, a $(C_3–C_{11})$cycloalkyl-alkyl group, an acyl group, an optionally substituted aryl group or an optionally substituted arylalkyl group, or Ra and Rb form together with the nitrogen atom carrying them a pyrrolyl, piperidinyl or piperazinyl group, it being possible for each of those cyclic groups to be optionally substituted, or two adjacent groups $R_2$, $R_3$, $R_4$ and $R_5$ form together with the carbon atoms carrying them a group —O—$(CH_2)_t$—O, t being an integer from 1 to 3 inclusive, $R_{60}$, $R_{70n}$, $R_{80}$ and $R_{90}$ each independently of the others represents a hydrogen atom, a hydroxy group, an alkoxy group, or a group O—(CO)—X or O—(CO)—NXW wherein X and W each independently of the other represents an alkyl group, an alkenyl group, an alkynyl group, a $(C_3–C_{11})$cycloalkyl group, a $(C_3–C_{11})$ cycloalkyl-alkyl group, an optionally substituted aryl group or an optionally substituted arylalkyl group, $R_{61}$, $R_{71n}$, $R_{81}$ and $R_{91}$ each independently of the others represents a hydrogen atom, an alkyl group, an alkenyl group or an alkynyl group, or, taken in pairs on adjacent carbon atoms, together form a bond or an oxirane group, or two geminal groups ($R_{60}$ and $R_{61}$) and/or ($R_{70n}$ and $R_{71n}$) and/or ($R_{80}$ and $R_{81}$) and/or ($R_{90}$ and $R_{91}$) together form an oxo group or a group —O—$(CH_2)_{t1}$—O, $t_1$ being an integer from 1 to 3 inclusive, with the proviso that $R_{60}$, $R_{61}$, $R_{70n}$, $R_{71n}$, $R_{80}$, $R_{81}$, $R_{90}$ and $R_{91}$ do not all represent a hydrogen atom, their enantiomers, diastereoisomers, and addition salts thereof with a pharmaceutically acceptable acid or base, it being understood that the term "alkyl" denotes a linear or branched chain having from 1 to 6 carbon atoms, the term "alkenyl" denotes a linear or branched chain having from 2 to 6 carbon atoms and containing from 1 to 3 double bonds, the term "alkynyl" denotes a linear or branched chain having from 2 to 6 carbon atoms and containing from 1 to 3 triple bonds, the term "alkoxy" denotes a linear or branched alkyl-oxy radical containing from 1 to 6 carbon atoms, the term "acyl" denotes a linear or branched alkyl-carbonyl radical containing from 1 to 6 carbon atoms, the term "aryl" represents a phenyl or naphthyl group, the expression "substituted" when used in relation to aryl or arylalkyl groups means that the groups in question are substituted by one or more halogen atoms, and/or groups alkyl, alkoxy, hydroxy, cyano, nitro, and/or amino (optionally substituted by one or two alkyl groups), the expression "substituted" when used in relation to pyrrolyl, piperidinyl or piperazinyl groups means that the groups in question are substituted by one or more alkyl, alkoxy, aryl, arylalkyl, aryloxy and/or aryloxyalkyl groups.

An advantageous aspect of the invention relates to compounds of formula (I) wherein $R_{60}$ represents a hydroxy group and $R_{61}$ represents an alkyl group (for example ethyl).

Another advantageous aspect of the invention relates to compounds of formula (I) wherein $R_{80}$ and $R_{81}$ together form an oxo group, or $R_{90}$ and $R_{91}$ together form an oxo group, or $R_{80}$ with $R_{81}$ and $R_{90}$ with $R_{91}$ form two oxo groups.

Preferred compounds of formula (I) are those wherein $R_1$ represents a hydrogen atom.

Other preferred compounds of formula (I) are those wherein $R_2$, $R_3$, $R_4$ and $R_5$ are selected from a hydrogen atom, a halogen atom, an alkyl group and an alkoxy group, or two of those groups, when bonded to two adjacent carbon atoms, together form a methylenedioxy or ethylenedioxy group (preferably methylenedioxy). Among those compounds, preference is given to those wherein each of $R_2$ and $R_5$ represents a hydrogen atom.

An especially advantageous aspect of the invention relates to compounds of formula (I) wherein each of $R_2$ and $R_5$ represents a hydrogen atom, $R_3$ and $R_4$ are selected from a hydrogen atom, a halogen atom, an alkyl group and an alkoxy group, or together form a methylenedioxy group, $R_{60}$, $R_{70}$, $R_{80}$ and $R_{90}$ each independently of the others represents a hydrogen atom, a hydroxy group or an alkoxy group, and $R_{61}$, $R_{71}$, $R_{81}$ and $R_{91}$ each independently of the others represents a hydrogen atom or an alkyl group, or, taken in pairs on adjacent carbon atoms, together form a bond or an oxirane group, or two geminal groups ($R_{60}$ and $R_{61}$) and/or ($R_{70n}$ and $R_{71}$) and/or ($R_{80}$ and $R_{81}$) and/or ($R_{90}$ and $R_{91}$) together form an oxo group.

The present invention relates also to a process for the preparation of compounds of formula (I), characterised in that there is used as starting material a compound of formula (II):

The present invention relates also to a process for the preparation of compounds of formula (I), characterised in that there is used as starting material a compound of formula (II):

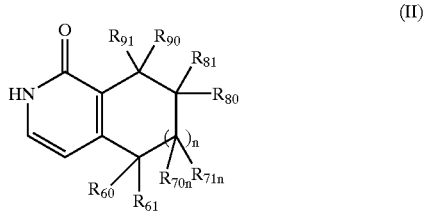

(II)

wherein n, $R_{60}$, $R_{61}$, $R_{70n}$, $R_{71n}$, $R_{80}$, $R_{81}$, $R_{90}$ and $R_{91}$ are as defined for formula (I), which is condensed, in a basic medium, with a compound of formula (III):

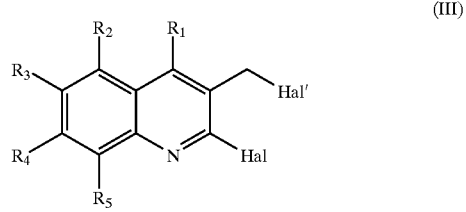

(III)

wherein $R_1$, $R_2$, $R_3$, $R_4$ and $R_5$ are as defined for formula (I), and Hal and Hal' each independently of the other represents a halogen atom, or, in accordance with the conditions of a Mitsunobu reaction, with a compound of formula (III'):

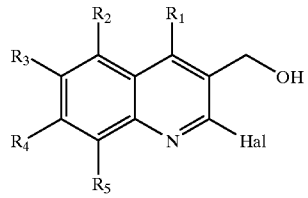

(III')

wherein $R_1$, $R_2$, $R_3$, $R_4$, $R_5$ and Hal are as defined hereinbefore, to yield a compound of formula (IV):

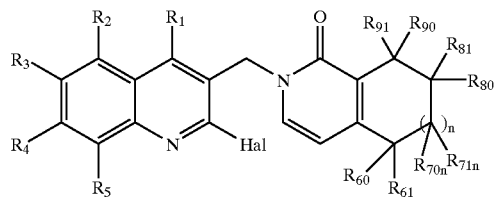

(IV)

wherein $R_1$, $R_2$, $R_3$, $R_4$, $R_5$, n, $R_{60}$, $R_{61}$, $R_{70n}$, $R_{71n}$, $R_{80}$, $R_{81}$, $R_{90}$, $R_{91}$ and Hal are as defined hereinbefore, which compound (IV) is subjected to an intramolecular cyclisation reaction of the "Heck" type catalysed by a palladium compound, to yield a compound of formula (I), it being understood, for the purpose of simplifying the above process, that the reactive groups present in $R_{60}$, $R_{61}$, $R_{70n}$, $R_{71n}$, $R_{80}$, $R_{81}$, $R_{90}$ and $R_{91}$ can be protected by conventional protecting groups and deprotected at the appropriate time point, that the hydroxy groups present in those same positions can be oxidised by conventional chemistry methods to oxo groups, and, conversely, the oxo groups present in those same positions can be reduced by conventional reducing agents at any appropriate time point in the synthesis, and that, when two of those groups together form a bond, the latter can be introduced at any time point deemed suitable by the person skilled in the art in order to facilitate the synthesis, which compounds of formula (I):

can be purified, if necessary, according to a conventional purification technique, are separated, where appropriate, into their stereoisomers according to a conventional separation technique, are converted, if desired, into addition salts thereof with a pharmaceutically acceptable acid or base.

The substrates of formulae (II) and (III) are commercial products or are prepared according to known procedures or using conventional reactions of organic chemistry. By way of illustration, there may be mentioned the processes described in J. Am. Chem. Soc., 1992, 37, 10971.

In particular, it is possible to prepare a substrate of formula (II'):

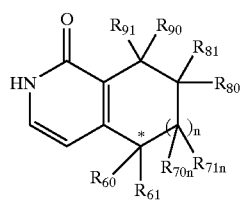

wherein n, $R_{60}$, $R_{61}$, $R_{70n}$, $R_{71n}$, $R_{80}$, $R_{81}$, $R_{90}$ and $R_{91}$ are as defined for formula (I) and * indicates that the carbon atom carrying the groups $R_{60}$ and $R_{61}$ has a fixed configuration (R) or (S), in order to obtain, according to the process described hereinbefore, a compound of formula (I'):

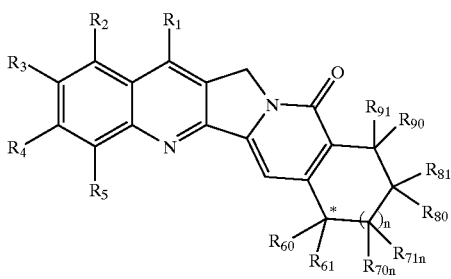

wherein $R_1$, $R_2$, $R_3$, $R_4$, $R_5$, n, $R_{60}$, $R_{61}$, $R_{70n}$, $R_{71n}$, $R_{80}$, $R_{81}$, $R_{90}$ and $R_{91}$ are as defined for formula (I) and * indicates that the configuration of the carbon atom is fixed.

Among the pharmaceutical compositions according to the invention, there may be mentioned more especially those that are suitable for oral, parenteral or nasal administration, tablets or dragees, sublingual tablets, gelatin capsules, lozenges, suppositories, creams, ointments, dermal gels, etc.

The useful dosage varies according to the age and weight of the patient, the nature and severity of the disorder and the route of administration, which may be oral, nasal, rectal or parenteral. The unit dose generally ranges from 0.1 to 500 mg for a treatment in from 1 to 3 administrations per 24 hours.

The following Examples illustrate the invention but do not limit it in any way.

The starting materials used are known products or are prepared according to known procedures.

The structures of the compounds described in the Examples and the Preparations were determined according to the usual spectrophotometric techniques (infrared, NMR, mass spectrometry, etc.).

Preparation A: 7-Hydroxy-6,7-dihydro-1H-cyclopenta[c]pyridine-1,5(2H)-dione

Step 1: 4-(1-Ethoxyvinyl)-2-fluoro-3-pyridinecarbaldehyde

There are mixed in succession 8 g (31.9 mmol) of 2-fluoro-4-iodo-3-pyridinecarbaldehyde (described in J.O.C, 1993, 58, pp. 7832), 12.7 g (35.96 mmol) of 1-ethoxyvinyltributyltin and 740 mg of tetrakis(triphenylphosphine)palladium (2% molar) in 280 ml of dioxane. The reaction mixture is heated at reflux until the starting material has disappeared completely. After returning to room temperature a solution of potassium fluoride is added to the reaction mixture. Vigorous stirring is maintained for 10 minutes in order to cause precipitation of the tributyltin fluoride, which is filtered off. The filtrate is plunged into a sodium chloride solution. The aqueous phase is extracted 3 times with dichloromethane and then the organic phases are combined, dried over magnesium sulphate, concentrated and purified by chromatography over a silica column, using a dichloromethane/cyclohexane mixture (95/5) as eluant to yield the expected product.

Step 2: 7-Hydroxy-6,7-dihydro-1H-cyclopenta[c]pyridine-1,5(2H)-dione

A mixture of 770 g (3.93 mmol) of the compound described in the preceding Step in 51 ml (102.1 mmol) of 2N hydrochloric acid is refluxed with air cooling for 2 hours, cooled and then concentrated. The resulting residue is washed in acetone, filtered and then recrystallised from isopropanol to yield the expected product.

Melting point: 200° C. (isopropanol)

Preparation B: 5-Ethyl-5,7-dihydroxy-2,5,6,7-tetrahydro-1H-cyclopenta[c]-pyridin-1-one Step 1: 1-Fluoro-7-hydroxy-6,7-dihydro-5H-cyclopenta[c]pyridin-5-one The process used is identical to that described in Preparation A, Step 1, using a dichloromethane/methanol mixture as eluant in the course of the purification. The resulting residue is stirred at room temperature for 3 hours in a solution of 16 ml of trifluoroacetic acid, 90 ml of acetonitrile and 35 ml of water. The reaction mixture is then neutralised with an aqueous $K_2CO_3$ solution and extracted 3 times with dichloromethane. The combined organic phases are dried over magnesium sulphate, filtered, concentrated and purified by chromatography over a silica column (eluant: dichloromethane/methanol 99.5/0.5) to obtain the expected compound.

Step 2: 5,7-Dihydroxy-5-ethyl-1-fluoro-6-6,7-dihydro-1H-cyclopenta[c]pyridine

At –30° C., 1.6 ml (4.7 mmol) of a solution of 3M ethylmagnesium bromide in ether are added dropwise to a solution of 350 mg (2.1 mmol) of the compound described in the preceding Step in 60 ml of ether. The reaction mixture is stirred at –30° C. for 3 hours before being hydrolysed with a saturated ammonium chloride solution. The organic phase is decanted, the aqueous phase is extracted 3 times with ethyl acetate and then the combined organic phases are dried over magnesium sulphate and filtered, concentrated, and purified by chromatography over a silica column (eluant: dichloromethane/acetone, 95/5) to yield the expected product.

Step 3: 5-Ethyl-5,7-dihydroxy-2,5,6,7-tetrahydro-1H-cyclopenta[c]pyridin-1-one

The expected product is obtained according to the process described in Step 2 of Preparation A using the compound described in the preceding Step as starting material.

Preparation C: 5-Ethyl-5,6-dihydroxy-2,5-dihydro-1H-cyclopenta[c]pyridin-1-one 0.5 g of sodium borohydride (13.20 mmol) is added at room temperature to a solution of 2 g of the product described in Preparation F (9.65 mmol) in 20 ml of methanol. After stirring for 30 minutes at room temperature, 20 ml of an aqueous saturated sodium hydrogen carbonate solution are added. The mixture is extracted with ethyl acetate. The organic phases are dried over magnesium sulphate, filtered and concentrated in vacuo to obtain the expected compound.

Preparation D: 5-Ethyl-5-methoxymethoxy-2H,5H-[2]pyridine-1,6,7-trione

A solution of 2.35 g (21.2 mmol) of selenium oxide in 3 ml of water is added to a solution of 3 g (10.6 mmol) of the compound prepared in Step 3 of Preparation F in 130 ml of dioxane. The reaction mixture is heated at 60° C. for 48 hours. The reaction mixture is filtered, the filtrate is concentrated in vacuo and the residue is taken up in ethyl acetate. The expected product is obtained by filtering off the precipitate.

Preparation E: 5-Ethyl-5-hydroxy-5,6-dihydro-1H-cyclopenta[c]pyridine-1,7-(2H)-dione Step 1: 5-Ethyl-1-fluoro-5-hydroxy-1,2,5,6-tetrahydro-7H-cyclopenta[c]pyridin-7-one 3 g of Celite, 4 Å molecular sieve, and then, in small fractions, 3.6 g (16.7 mmol) of pyridinium chlorochromate are added, in succession, to a solution, stirred at 0° C., of 3 g (15.2 mmol) of the compound described in Step 2 of Preparation B in a mixture of dichloromethane/acetone (15/1 v/v). The reaction mixture is stirred at room temperature for 20 hours and filtered, the solid is washed 3 times with 50 ml of a dichloromethane/acetone mixture (50/50 v/v) each time, and the filtrate is concentrated in vacuo. The resulting residue is purified by chromatography over silica (eluant: dichloromethane/acetone 85/15) to yield the expected product.

Step 2: 5-Ethyl-5-hydroxy-5,6-dihydro-1H-cyclopenta[c]pyridine-1,7(2H)-dione

A suspension of 3.5 g (17.7 mmol) of the compound described in the preceding Step in 360 ml of 1N hydrochloric acid is heated at 80° C. for 1 hour. The reaction mixture is concentrated in vacuo. The solid residue is stirred in ether, and the precipitate is filtered off and dried to yield the expected product.

Preparation F: 5-Ethyl-6-[2-(1,3-dioxolan)yl]-5-hydroxy-5,7-dihydro-1H-cyclopenta[c]pyridin-1(2H)-one Step 1: Methyl 2-(2-fluoro-3-methyl-4-pyridinyl)-2-hydroxybutanoate 6.9 ml (11 mmol) of 1.6M butyllithium in hexane are added dropwise to a solution, stirred at −78° C. of 2.6 g (11 mmol) of 2-fluoro-4-iodo-3-methylpyridine (described in J.O.C., 1993, 58, pp. 7832) in 100 ml of THF. The reaction mixture is then stirred for 10 minutes at −78° C. before the addition of a solution of 1.5 g (12.9 mmol) of methyl 2-oxo-butyrate in 20 ml of THF. The reaction mixture is stirred for 10 minutes at −78° C., and then hydrolysed with a mixture of water/THF. The aqueous phase is decanted and then extracted 3 times with 50 ml of methyl acetate each time. The combined organic phases are dried, concentrated and purified by chromatography over silica (eluant dichloromethane/acetone 95/5) to yield the expected product.

Step 2: Methyl 2-(2-fluoro-3-methyl-4-pyridinyl)-2-methoxymethoxylbutanoate 260 mg (8.8 mmol) of an 80% suspension of sodium hydride in mineral oil are added in small fractions to a solution, stirred at 0° C., of 2 g (8.8 mmol) of the compound described in the preceding Step in 60 ml of THF. Once the addition is complete, the mixture is stirred at room temperature until the evolution of gas has ceased. A solution of 0.94 g (11.6 mmol) of chloromethyl methyl ether in 10 ml of THF is then added dropwise and the mixture is stirred at room temperature for 2 hours, hydrolysed with 2N hydrochloric acid and decanted. The aqueous phase is extracted with dichloromethane, and the combined organic phases are dried over magnesium sulphate and concentrated. The expected product is obtained by chromatography of the residue over silica (eluant: dichloromethane/acetone 95/5).

Step 3: 5-Ethyl-1-fluoro-5-(methoxymethoxy)-5,7-dihydro-6H-cyclopenta[c]-pyridin-6-one 55 ml (88.5 mmol) of a 1.6M butyllithium solution in hexane are added to a solution, stirred at 0° C., of 9 g (88.5 mmol) of diisopropylamine in 160 ml of THF. The mixture is stirred for ½ hour at 0° C. before the dropwise addition, at that temperature, of 15.8 g (88.5 mmol) of hexamethylphosphoramide. The mixture is again stirred at 0° C. for ½ hour before the dropwise addition of a solution of 5.3 g (19.5 mmol) of the compound described in the preceding Step in 40 ml of THF. The reaction mixture is stirred for 1 hour at room temperature before being hydrolysed with water. The aqueous phase is extracted with ethyl acetate, and the organic phase is washed with a 2N hydrochloric acid solution and then with a saturated sodium chloride solution, dried over magnesium sulphate and concentrated. The resulting residue is purified by chromatography over silica (eluant dichloromethane/acetone 95/5) to yield the expected product.

Step 4: 5-Ethyl-5-hydroxy-5,7-dihydro-1H-cyclopenta[c]pyridine-1,6(2H)-dione

A suspension of 1 g (4.18 mmol) of the compound described in the preceding Step in 40 ml of 3N hydrochloric acid is refluxed for 1 hour. The mixture is concentrated, the resulting residue is taken up in ether and decanted and, after the addition of acetonitrile, the resulting solid is filtered off and washed with ether to yield the expected product.

Step 5: 5-Ethyl-6-[2-(1,3-dioxolan)yl]-5-hydroxy-5,7-dihydro-1H-cyclopenta[c]-pyridin-1

A suspension of 2.5 g (13 mmol) of the compound prepared in the preceding Step, 15 ml of ethylene glycol and 40 mg of para-toluenesulphonic acid in 40 ml of toluene is refluxed for 4 hours. The mixture is concentrated in vacuo, the black residue is taken up in ethyl acetate, and the resulting white precipitate is filtered off to yield the expected product.

Preparation G: 5-Ethyl-5-hydroxy-7,8-dihydro-1,6(2H,5H)-isoquinolinedione

Step 1: 3-(1,3-Dioxolan-2-yl)-2-fluoro-4-iodopyridine

In a three-necked flask equipped with a Dean Stark apparatus, a mixture of 5.1 g (20.3 mmol) of 2-fluoro-4-iodo-3-pyridinecarbaldehyde, 1.4 g (22.3 mmol) of ethane-1,2-diol, and 50 mg of para-toluenesulphonic acid in 100 ml of toluene is heated at reflux. When the theoretical amount of water has been collected, the reaction mixture is cooled to room temperature, washed with a saturated sodium hydrogen carbonate solution and dried over magnesium sulphate. The expected product is obtained by concentration.

Step 2: Methyl 2-[3-(1,3-dioxolan-2-yl)-2-fluoro-4-pyridinyl]-2-hydroxybutanoate 6.9 ml (11 mmol) of 1.6M butyllithium in hexane are added dropwise to a solution, stirred at −78° C. under an argon atmosphere, of 3.1 g (11 mmol) of 3-(1,3-dioxolan-2-yl)-2-fluoro-4-iodopyridine in 100 ml of THF. The reaction mixture is then stirred for 10 minutes at −78° C. before the dropwise addition of a solution of 1.5 g (13 mmol) of methyl 2-oxo-butyrate in 20 ml of THF. The mixture is stirred for 3 hours at −78° C., hydrolysed with a mixture of water/THF, and decanted. The aqueous phase is extracted 3 times with 50 ml of ethyl acetate each time, and the combined organic phases are dried over magnesium sulphate and then concentrated. The expected product is obtained by purification of the residue by chromatography over silica (eluant: dichloromethane/acetone 95/5).

Step 3: Methyl 2-(benzyloxy)-2-[3-(1,3-dioxolan-2-yl)-2-fluoro-4-pyridinyl]-butanoate A solution of 14.8 g (51.8 mmol) of the compound described in the preceding Step in 100 ml of DMF is added dropwise to a suspension, stirred at 0° C., of 2 g (67.4 mmol) of 80% sodium hydride in 100 ml of DMF. Once the addition is complete, the mixture is stirred for ½ hour before the addition, at that temperature, in succession, of 0.15 g of tetrabutylammonium iodide, and then 9.8 g (57.1 mmol) of benzyl bromide dissolved in 50 ml of DMF. The mixture is stirred for 2 hours at 0° C., plunged into ice-cold water and extracted with ethyl acetate, and the organic phase is washed with water and then dried over magnesium sulphate and concentrated. The expected product is obtained by purification of the residue over silica gel (eluant: dichloromethane/acetone 95/5).

Step 4: Methyl 2-(benzyloxy)-2-[3-(dimethoxymethyl)-2-fluoro-4-pyridinyl]-butanoate A solution of 3.4 g (9 mmol) of the ester described in the preceding Step and 0.1 g of para-toluenesulphonic acid in 250 ml of methanol is stirred at room temperature for 24 hours. The solvent is concentrated. The crude residue is taken up in ethyl acetate, and the organic phase is neutralised with a saturated sodium hydrogen carbonate solution, washed with water and dried over magnesium sulphate. The expected product is obtained by concentration.

Step 5: Methyl 2-(benzyloxy)-2-(2-fluoro-3-formyl-4-pyridinyl)butanoate

A solution of 20.3 g (0.178 mmol) of trifluoroacetic acid in 20 ml of water is added to a solution of 3.3 g (8.75 mmol) of the ester described in the preceding Step in 60 ml of dichloromethane. The reaction mixture is stirred for 18 hours at room temperature and decanted. The aqueous phase is extracted with dichloromethane, and the combined organic phases are washed with a sodium hydrogen carbonate solution and then with salt water, and dried over magnesium sulphate. The expected product is obtained by concentration.

Step 6: Methyl 3-{4-[1-(benzyloxy)-1-(methoxycarbonyl)propyl]-2-fluoro-3-pyridinyl}-2-acrylate A mixture of 21 g (63.3 mmol) of the product described in the preceding Step and 22.3 g (63.3 mmol) of carboxymethylenetriphenylphosphorane in 1 litre of toluene is heated at reflux for 2 hours 30 minutes. After returning to room temperature, the solvent is removed by evaporation, the residue is crystallised from ether, the crystals are filtered off and the filtrate is concentrated in cacao. The residue is purified by chromatography over silica gel (eluant: dichloromethane/acetone, from 100/0 to 96/4) to yield the expected product.

Step 7: Methyl 2-(benzyloxy)-2-{2-fluoro-3-[2-(methoxycarbonyl)ethyl]-4-pyridinyl}butanoate 2.5 g (10.5 mmol) of cobalt chloride are added to a solution, stirred at 0° C., of 16.3 g (42 mmol) of the compound described in the preceding Step in 900 ml of methanol. The reaction mixture is stirred at 0° C. for 10 minutes, and then 3.2 g (84 mmol) of sodium borohydride are added in small fractions. The mixture is then concentrated in vacuo, the residue is taken up in ethyl acetate, and the organic phase is washed with water, dried over magnesium sulphate, filtered over Celite and concentrated to yield the expected product.

Step 8: Methyl 2-(benzyloxy)-2-[3-(3-methoxy-3-oxopropyl)-2-oxo-1,2-dihydro-4-pyridinyl]butanoate 257 ml of a Normal solution of hydrochloric acid are added to a solution of 5 g (12.83 mmol) of the compound described in the preceding Step in 80 ml of dioxane. The reaction mixture is then refluxed for 1 hour 30 minutes. After returning to room temperature, the mixture is concentrated in vacuo, and the residue is purified by chromatography over silica gel (eluant: dichloromethane 97/methanol 3) to yield the expected product.

Step 9: Methyl 5-(benzyloxy)-5-ethyl-6-hydroxy-1-oxo-1,2,5,8-tetrahydro-7-isoquinolinecarboxylate 200 ml of a solution of 4.7 g (12.1 mmol) of the compound described in the preceding Step in THF are added dropwise to a suspension, stirred at 0° C., of 0.8 g (26.7 mmol) of 80% sodium hydride in 50 ml of THF. The mixture is then stirred for 15 minutes at 0° C., for 15 minutes at room temperature and then for 1 hour at reflux before being hydrolysed at 0° C. with a Normal solution of hydrochloric acid until the pH is neutral. The aqueous phase is extracted with dichloromethane. The organic phase is washed with water, dried over magnesium sulphate and concentrated to yield the expected product.

Step 10: 5-(Benzyloxy)-5-ethyl-7,8-dihydro-1,6(2H, 5H)-isoquinolinedione

A suspension of 16.1 g (45.3 mmol) of the compound described in the preceding Step in 60 ml of a Normal solution of potassium hydroxide is heated at reflux for 30 minutes. The reaction mixture is neutralised at 0° C. by the dropwise addition of a 2N solution of hydrochloric acid and then extracted with dichloromethane. The organic phase is filtered, dried over magnesium sulphate and concentrated. The expected product is obtained after purification by chromatography over silica gel (eluant: dichloromethane/methanol from 100/0 to 96/4).

Step 11: 5-Ethyl-5-hydroxy-7,8-dihydro-1,6(2H,5H)-isoquinolinedione

A solution of 7.9 g (26.56 mmol) of the compound described in the preceding Step in 800 ml of methanol is stirred at atmospheric pressure and room temperature under a hydrogen atmosphere in the presence of 0.8 g of 10% palladium-on-carbon. After absorption of the theoretical amount of hydrogen (approximately 3 hours 30 minutes), the catalyst is removed by filtration, the filtrate is concentrated, and the expected product is obtained by cristallisation of the residue from ether.

Preparation H: 5-Ethyl-5-hydroxy-7-methoxy-2,5,6,7-tetrahydro-1H-cyclopenta[c]pyridin-1-one A suspension of 2.2 g (11.95 mmol) of the compound described in Step 2 of Preparation B in 220 ml of IN hydrochloric acid is heated at 80° C. for 1 hour 30 minutes. The reaction mixture is concentrated, and the residue is purified by chromatography over silica gel (eluant: dichloromethane/methanol 95/5) to yield the expected compound.

Preparation I: (5S)-5-Ethyl-5-hydroxy-5,7-1H-cyclopenta[c]pyridine-1,6-(2H)-dione Step 1: 3-(3-Allyl-2-fluoro-4-pyridinyl)-3-pentanol 27 ml (43.3 mmol) of 1.6M butyllithium in hexane are added, at −75° C., to a solution of 11.4 g (43.3 mmol) of 3-allyl-2-fluoro-4-iodopyridine (prepared according to the process described in J.O.C., 1993, 58, pp. 7832) in 250 ml of THF. After 30 minutes' stirring at −75° C., a solution of 4.6 ml of 3-pentanone in 100 ml of THF is added dropwise. The reaction mixture is stirred for 6 hours at −75° C. After returning to room temperature, the mixture is hydrolysed with 100 ml of water and extracted with ethyl acetate. The organic phase is dried, concentrated and purified by chromatography over silica (eluant: cyclohexane/ethyl acetate 8/2) to yield the expected product.

Step 2: 3-Allyl-4-(1-ethyl-1-propenyl)-2-fluoropyridine 17.6 ml (126 mmol) of triethylamine are added to a solution of 1.4 g (6.3 mmol) of the compound described in the preceding Step in 50 ml of dichloromethane. The temperature is reduced to 0° C. and 2.3 ml (31.5 mmol) of thionyl chloride in 20 ml of dichloromethane are added. After 5 minutes' stirring at room temperature, the reaction mixture is poured into 70 ml of water and then extracted with dichloromethane. The organic phase is dried, concentrated and purified by chromatography over silica (eluant: cyclohexane/ethyl acetate 9/1) to yield the expected product.

Step 3: 5-Ethyl-1-fluoro-7H-cyclopenta[c]pyridine

A mixture of 1 g (4.87 mmol) of the compound described in the preceding Step and 200 mg (0.24 mmol) of ruthenium (IV) bis(tricyclohexylphosphine)benzylidene dichloride are dissolved in 20 ml of toluene. The solution is stirred at room temperature for 15 hours and then filtered. The filtrate is concentrated and purified by chromatography over silica (eluant: cyclohexane/ethyl acetate 8/2) to yield the expected product.

Step 4: (5S)-5-Ethyl-1-fluoro-6,7-dihydro-5H-cyclopenta[c]pyridine-5,6-diol 50 ml of distilled water, 9 g (27.3 mmol) of potassium ferricyanide, 3.6 g (28 mmol) of potassium carbonate, 10 mg (0.03 mmol) of potassium osmate dihydrate and 0.85 g (8.9 mmol) of methanesulphonamide are added, in succession, to a solution of 80 mg (0.01 mmol) of (DHQD)$_2$-Pyr in 50 ml of tert-butyl alcohol After 3 minutes' stirring at room temperature, the mixture is cooled to 0° C. and a solution of 1.4 g (8.6 mmol) of the compound described in the preceding Step in 5 ml of tert-butyl alcohol is added. The reaction mixture is stirred for 2 days at 0° C. The mixture is extracted with ethyl acetate, and the organic phases are dried, concentrated and purified by chromatography over silica (eluant: cyclohexane/ethyl acetate 5/5) to yield the expected product.

Step 5: (5S)-5-Ethyl-1-fluoro-5-hydroxy-5,7-dihydro-6H-cyclopenta[c]pyridin-6-one 0.82 ml of dimethyl sulphoxide is added, at −78° C., to a mixture of 1.1 g (5.5 mmol) of the compound described in the preceding Step and 0.48 ml (5.5 mmol) of oxalyl chloride in 100 ml of dichloromethane. After 20 minutes at −78° C., 4 ml (28.4 mmol) of triethylamine are added and the mixture is stirred for 15 minutes at low temperature, and returned to room temperature. The reaction mixture is hydrolysed with 100 ml of water and extracted with dichloromethane. The organic phase is washed with an aqueous 1% hydrochloric acid solution and then with an aqueous saturated sodium hydrogen carbonate solution. Drying and concentration yield the expected product.

Step 6: (5S)-5-Ethyl-5-hydroxy-5,7-1H-cyclopenta[c]pyridine-1,6-(2H)-dione

The expected product is obtained according to the process described in Step 4 of Preparation F using the compound described in the preceding Step as starting material.

Preparation J: 5-Ethyl-5-hydroxy-5,8-dihydro-1-(2H)-isoquinolinone

Step 1: 1-(3-Allyl-2-fluoro-4-pyridinyl)-1-propanol

The expected product is obtained according to the process described in Step 1 of Preparation I, replacing 3-pentanone by propanal.

Step 2: 1-(3-Allyl-2-fluoro-4-pyridinyl)-1-propanone 0.5 g of Celite, 0.2 g of 4 Å molecular sieve and 0.58 g (2.69 mmol) of pyridinium chlorochromate are added, at 0° C., to a solution of 0.5 g (2.56 mmol) of the compound described in the preceding Step in 25 ml of dichloromethane. After returning to room temperature, the mixture is stirred for 15 hours and then filtered. The filtrate is concentrated and purified by chromatography over silica (eluant: dichloromethane/acetone, 97/3) to yield the expected product.

Step 3: 3-(3-Allyl-2-fluoro-4-pyridinyl)-1-penten-3-ol 2.1 ml of a 1 M solution of vinylmagnesium bromide in THF are added at 0° C. to a solution of 0.32 g (1.66 mmol) of the compound described in the preceding Step in 10 ml of THF. After 45 minutes' stirring at 0° C., the mixture is hydrolysed with a 1M hydrochloric acid solution, and extracted with ether. The organic phases are washed with an aqueous saturated sodium hydrogen carbonate solution, dried over magnesium sulphate and concentrated. The residue is purified by chromatography over silica gel (eluant: dichloromethane/acetone, 95/5) to yield the expected product.

Step 4: 5-Ethyl-1-fluoro-5,8-dihydro-5-isoquinolinol

The expected product is obtained according to the process described in Step 3 of Preparation I, using the compound described in the preceding Step as starting material.

Step 5: 5-Ethyl-5-hydroxy-5,8-dihydro-1-(2H)-isoquinolinone 5 g (45 mmol) of potassium tert-butylate are added to a solution of 0.5 g (2.59 mmol) of the product described in the preceding Step in 25 ml of tert-butanol. After 16 hours' stirring at reflux, the reaction mixture is cooled and hydrolysed with 50 ml of water and rendered acidic with a 2M hydrochloric acid solution. The resulting precipitate is filtered off and dried to yield the expected product.

Preparation K: 5-Ethyl-5-hydroxy-5,8-dihydro-1,6,7-(2H)-isoquinolinetrione

Step 1: 5-Ethyl-5,6,7-trihydroxy-5,6,7,8-tetrahydro-1-(2H)-isoquinolinone 4 ml of a 2.5% solution of osmium tetroxide in tert-butanol and then 1.5 g of N-methyl-morpholine N-oxide (12.8 mmol) are added at room temperature to a solution of 2 g (10.4 mmol) of the compound described in Preparation J in a mixture of 70 ml of dioxane and 30 ml of water. After stirring overnight at room temperature, the mixture is extracted with ethyl acetate, and the organic phases are dried and concentrated to yield the expected product.

Step 2: 5-Ethyl-5-hydroxy-5,8-dihydro-1,6,7-(2H)-isoquinolinetrione 1.30 ml of dimethyl sulphoxide (18.2 mmol) are added at −78° C. to a mixture of 1 g (4.44 mmol) of the compound described in the preceding Step and 0.78 ml (8.88 mmol) of oxalyl chloride in 100 ml of dioxane. After 30 minutes at −78° C., 6 ml (42.6 mmol) of triethylamine are added. After 15 minutes' at −78° C., the mixture is returned to room temperature. The reaction mixture is hydrolysed with 100 ml of water and extracted with ethyl acetate. The organic phase is washed with a 1N hydrochloric acid solution and then with an aqueous saturated sodium hydrogen carbonate solution. Drying and concentration yield the expected product.

Preparation L: 7-Ethyl-7-hydroxy-2,4,7,7a-tetrahydroxireno[2,3-g]isoquinolin-3(1aH)-one 1.17 g (6.8 mmol) of m-chloroperbenzoic acid are added at 0° C. to a solution of 1 g (5.2 mmol) of the product described in Preparation J in 100 ml of dioxane. After stirring for 1 hour at room temperature, the solution is diluted with 100 ml of ethyl acetate and washed with an aqueous saturated sodium hydrogen carbonate solution. Drying over magnesium sulphate and removal of the solvents by evaporation yield the expected product.

Preparation M: 5-Ethyl-5-hydroxy-2,5,6,9-tetrahydro-1H-cyclohepta[c]pyridin-1-one The expected product is obtained according to the process described in Preparation J, replacing vinylmagnesium bromide in Step 3 by allylmagnesium bromide.

Preparation N: 5-Ethyl-5-hydroxy-5,6,8,9-tetrahydro-1H-cyclohepta[c]-pyridine-1,7(2H)-dione Step 1: (2-Fluoro-4-iodo-3-pyridinyl)methanol 0.72 g (19.2 mmol) of sodium borohydride is added to a solution of 4 g (16 mmol) of 2-fluoro-4-iodo-3-pyridinecarbaldehyde (described in J.O.C., 1993, 58, pp. 7832) in 100 ml of tetrahydrofuran. The mixture is stirred at room temperature for 4 hours and then hydrolysed. The reaction mixture is extracted with ethyl acetate. The organic phases are dried and concentrated to yield the expected product.

Step 2: 2-Fluoro-4-iodo-3-[(2-methoxyethoxy)methyl]pyridine

A solution of 2.1 g (16.8 mmol) of chloromethoxy-2-methoxyethane in 10 ml of dichloromethane, and then a solution of 2.2 g (16.8 mmol) of ethyldiisopropylamine and 180 mg (1.4 mmol) of 4-dimethylaminopyridine in 10 ml of dichloromethane are added, in succession, to a solution of 3.5 g (14 mmol) of the compound described in the preceding Step in 20 ml of dichloromethane. The mixture is stirred for 18 hours and then hydrolysed. The mixture is extracted with dichloromethane, and the organic phase is washed with an aqueous saturated sodium chloride solution until neutral, dried and concentrated to yield the expected product.

Step 3: 1-{2-Fluoro-3-[(2-methoxyethoxy)methyl]-4-pyridinyl}-1-propanol

The expected product is obtained according to the process described in Step 2 of Preparation G, using the compound described in the preceding Step as starting material and using propionaldehyde as electrophilic agent.

Step 4: 1-{2-Fluoro-3-[(2-methoxyethoxy)methyl]-4-pyridinyl}-1-propanone

The expected product is obtained according to the process described in Step 1 of Preparation E, using the compound described in the preceding Step as starting material.

Step 5: Methyl 3-{2-fluoro-3-[(2-methoxyethoxy)methyl]-4-pyridinyl}-3-hydroxypentanoate A solution of 3 g (10.2 mmol) of the compound described in the preceding Step and 5.1 g (33 mmol) of methyl bromoacetate in 40 ml of THF is added dropwise to a suspension in 5 ml of THF, at reflux, of 2.16 g (33 mmol) of zinc, previously activated by treatment with 6M hydrochloric acid, in such a manner as to maintain reflux. Once the addition is complete, the mixture is stirred at reflux for 1 hour, and then cooled and hydrolysed with an aqueous saturated ammonium choride solution. After extraction with ether, the organic phase is dried, concentrated and purified by chromatography over silica (eluant: dichloromethane/acetone, 95/5) to yield the expected product.

Step 6: Methyl 3-[2-fluoro-3-(hydroxymethyl)-4-pyridinyl]-3-hydroxypentanoate

A solution of 3.5 g (10.1 mmol) of the compound prepared in the preceding Step in 20 ml of THF and 20 ml of 2N HCl is stirred at room temperature for 3 hours. The reaction mixture is decanted, the aqueous phase is extracted with ethyl acetate, the combined organic phases are washed until neutral with an aqueous saturated sodium chloride solution and dried over magnesium sulphate, and the expected product is obtained by removal of the solvents by evaporation.

Step 7: Methyl 3-(2-fluoro-3-formyl-4-pyridinyl)-3-hydroxypentanoate 1.2 g (13.9 mmol) of manganese dioxide are added to a solution of 3 g (11.6 mmol) of the compound described in the preceding Step in 50 ml of dichloromethane. After 2 hours' stirring at room temperature, the reaction mixture is filtered over Celite, and the filtrate is concentrated to yield the expected product.

Step 8: Methyl 3-[4-(1-ethyl-1-hydroxy-3-methoxy-3-oxopropyl)-2-fluoro-3-pyridinyl]-2-acrylate The expected product is obtained according to the process described in Step 6 of Preparation G, using the compound described in the preceding Step as starting material.

Step 9: Methyl 3-[2-fluoro-3-(3-methoxy-3-oxopropyl)-4-pyridinyl]-3-hydroxypentanoate The expected product is obtained according to the process described in Step 7 of Preparation G, using the compound described in the preceding Step as starting material.

Step 10: Methyl 3-[2-fluoro-3-(3-methoxy-3-oxopropyl)-2-oxo-1,2-dihydro-4-pyridinyl]-3-trimethylsilyloxypentanoate A solution of 2.7 ml (15 mmol) of trimethylsilyl triflate in 5 ml of methylene chloride is added dropwise at 0° C. to a solution of 3.1 g (10 mmol) of the compound prepared in the preceding Step and 3 g (30 mmol) of triethylamine in 20 ml of methylene chloride. The reaction mixture is stirred for 2 hours at 0° C., and then hydrolysed with 20 ml of water. The organic phase is decanted and dried over magnesium sulphate. The expected product is obtained by removing the solvents by evaporation.

Step 11: Methyl 5-ethyl-1-fluoro-7-oxo-5-trimethylsilanyloxy-6,7,8,9-tetrahydro-5H-cyclohepta[c]pyridine-8-carboxylate The expected product is obtained according to the process described in Step 9 of Preparation G, using the compound described in the preceding Step as starting material.

Step 12: 5-Ethyl-5-hydroxy-5,6,8,9-tetrahydro-1H-cyclohepta[c]pyridine-1,7(2H)-dione A suspension of 1.7 g (5 mmol) of the compound prepared in the preceding Step in 20 ml of a Normal solution of potassium hydroxide is heated at reflux for 2 hours. The reaction mixture is cooled to room temperature, rendered acidic by the addition of 40 ml of a 6N hydrochloric acid solution and stirred at room temperature for 30 minutes and then at 80° C. for 1 hour. After cooling, the mixture is extracted with methylene chloride. The organic phase is dried over magnesium sulphate and concentrated to yield the expected compound.

Preparation O: 5-Ethyl-5-hydroxy-2,5,6,8-tetrahydro-1,7-isoquinolinedione 2 ml of boron trifluoride-diethyl ether complex (16.7 mmol) are added, at −78° C., to a solution of 1 g (4.8 mmol) of the product described in Preparation L in 100 ml of dioxane. After returning to room temperature, the mixture is stirred for 20 hours, and then poured into a mixture of ethyl acetate/water. The organic phases are dried over magnesium sulphate. Removal of the solvents by evaporation yields the expected product.

EXAMPLE 1

9-Hydroxy-9,12-dihydro-7H-cyclopenta[6,7]indolizino[1,2 -b]-quinoline-7,10(8H)-dione Step a: 2-[(2-Bromo-3-quinolinyl)methyl]-7-hydroxy-6,7-dihydro-1H-cyclopenta[c]pyridine-1,5(2H)-dione 0.6 mmol (18 mg) of NaH as an 80% dispersion in mineral oil is added in small fractions to a solution, stirred at 0° C. of 0.6 mmol (100 mg) of the compound described in Preparation A in 20 ml of a DME/DMF mixture (16/4 (v/v)). The mixture is stirred at 0° C. for 10 minutes before the addition, at that temperature, of 2.4 mmol (210 mg) of LiBr. After returning to room temperature, the reaction mixture is stirred for ¼ hour before the addition of 0.66 mmol (200 mg) of 2-bromo-3-bromomethylquinoline. The reaction mixture is then heated at 80° C. for 20 hours and, after returning to room temperature, subsequently poured into a large excess of water. The precipitate that forms is filtered off and washed with ether to yield the expected product.

Step b: 9-Hydroxy-9,12-dihydro-7H-cyclopenta[6,7]indolizino[1,2]quinoline-7,10(8H)-dione Under an inert atmosphere there are mixed, in succession, 0.98 mmol (380 mg) of the compound described in the preceding Step, 3.2 mmol (319 mg) of potassium acetate, 1.57 mmol (505 mg) of tetrabutylammonium bromide and 17 mmol (38 mg) of palladium acetate in 45 ml of acetonitrile. The mixture is then refluxed for 4 hours and subsequently filtered while hot. The residue is washed with a hot solution of dichloromethane and methanol. The filtrate is then concentrated and purified by chromatography over silica (eluant: dichloromethane/methanol 98/2) to yield the expected product.

Mass spectrum: LC-MS: m/z: 305 (MH$^+$); 287 (MH$^+$-H$_2$O)

EXAMPLE 2

7-Ethyl-7,8-dihydroxy-7,8,9,12-tetrahydro-10H-cyclopenta[6,7]-indolizino[1,2-b]quinolin-10-one The expected product is obtained according to the process described in Example 1, using the compound described in Preparation B as starting material.

EXAMPLE 3

7-Ethyl-7,8-dihydroxy-7,12-dihydro-10H-cyclopenta[6,7]indolizino-[1,2-b]quinolin-10-one The expected product is obtained according to the process described in Example 1, using the compound described in Preparation C as starting material.

EXAMPLE 4

7-Ethyl-7-hydroxy-7H-cyclopenta[6,7]indolizino[1,2-b]quinoline-8,9,10(12H)-trione The expected product is obtained according to the process described in Example 1, using the compound described in Preparation D as starting material.

EXAMPLE 5

7-Ethyl-7-hydroxy-7H-cyclopenta[6,7]indolizino[1,2-b]quinoline-9,10(8H,12H)-dione The expected product is obtained according to the process described in Example 1, using the compound described in Preparation E as starting material.

EXAMPLE 6a

7-Ethyl-7-hydroxy-8-[2-(1,3-dioxolan)yl]-9,12-dihydro-7H-cyclopenta[6,7]indolizino[1,2-b]quinolin-10-one The expected product is obtained according to the process described in Example 1, using the compound described in Preparation F as starting material.

Mass spectrum: (MH$^+$) m/z=377

EXAMPLE 6b

7-Ethyl-7-hydroxy-9,12-dihydro-7H-cyclopenta[6,7]indolizino-[1,2-b]quinoline-8,10-dione A solution of 1 g (2.66 mmol) of the compound prepared in Example 6a in 10 ml of trifluoroacetic acid and 1 ml of water is heated at 80° C. for 2 hours. The mixture is concentrated in vacuo, the residue is plunged into 20 ml of water, and the precipitate is filtered off, dried and taken up in 10 ml of hot alcohol. The expected product is obtained by filtration and drying of the insoluble product.

Mass spectrum: (MH$^+$) m/z=333

The compounds of Examples 9,10,11,12,13,14 and 15 were obtained in the same manner.

EXAMPLE 7

7-Ethyl-7-hydroxy-10,13-dihydrobenzo[6,7]indolizino[1,2-b]-quinoline-8,11(7H,9H)-dione The expected product is obtained according to the process described in Example 1, using the compound described in Preparation G as starting material.

Mass spectrum: (MH$^+$) m/z=347

EXAMPLE 8

7-Ethyl-7-hydroxy-9-methoxy-7,8,9,12-tetrahydro-10H-cyclopenta[6,7]indolizino[1,2-b]quinolin-10-one The expected product is obtained according to the process described in Example 1, using the compound described in Preparation H as starting material.

Mass spectrum: (MH$^+$) m/z=349

EXAMPLE 9

3-Chloro-7-ethyl-7-hydroxy-2-methyl-9,12-dihydro-7H-cyclopenta[6,7]indolizino[1,2-b]quinolin-8,10-one The expected product is obtained according to the process described in Example 6 (6a+6b), using the compound described in Preparation F as starting material, and replacing 2-bromo-3-bromomethylquinoline by 2-bromo-3-bromomethyl-7-chloro-6-methylquinoline.

Mass spectrum: (MH$^+$) m/z=381

EXAMPLE 10

2,3-Dimethyl-7-ethyl-7-hydroxy-9,12-dihydro-7H-cyclopenta[6,7]-indolizino[1,2-b]quinoline-8,10-dione The expected product is obtained according to the process described in Example 6 (6a+6b), using the compound described in Preparation F as starting material, and replacing 2-bromo-3-bromomethylquinoline by 2-bromo-3-bromomethyl-6,7-dimethylquinoline.

Mass spectrum:. (MH$^+$) m/z=361

EXAMPLE 11

7-Ethyl-7-hydroxy-2,3-methylenedioxy-9,12-dihydro-7H-cyclopenta[6,7]indolizino[1,2-b]quinoline-8,10-dione The expected product is obtained according to the process described in Example 6 (6a+6b), using the compound described in Preparation F as starting material, and replacing 2-bromo-3-bromomethylquinoline by 2-bromo-3-bromomethyl-6,7-methylenedioxy-quinoline.

Mass spectrum: (MH$^+$) m/z=377

EXAMPLE 12

2,3-Difluoro-7-ethyl-7-hydroxy-9,12-dihydro-7H-cyclopenta[6,7]-indolizino[1,2-b]quinoline-8,10-dione The expected product is obtained according to the process described in Example 6 (6a+6b), using the compound described in Preparation F as starting material, and replacing 2-bromo-3-bromomethylquinoline by 2-bromo-3-bromomethyl-6,7-difluoroquinoline.

Mass spectrum: (MH⁺) m/z=369

EXAMPLE 13

2-Chloro-7-ethyl-7-hydroxy-9,12-dihydro-7H-cyclopenta[6,7]-indolizino[1,2-b]quinoline-8,10-dione The expected product is obtained according to the process described in Example 6 (6a+6b), using the compound described in Preparation F as starting material, and replacing 2-bromo-3-bromomethylquinoline by 2-bromo-3-bromomethyl-6-chloroquinoline.

Mass spectrum: (MH⁺) m/z=367

EXAMPLE 14

7-Ethyl-7-hydroxy-2-methoxy-9,12-dihydro-7H-cyclopenta[6,7]-indolizino[1,2-b]quinoline-8,10-dione The expected product is obtained according to the process described in Example 6 (6a+6b), using the compound described in Preparation F as starting material and replacing 2-bromo-3-bromomethylquinoline by 2-bromo-3-bromomethyl-6-methoxyquinoline.

Mass spectrum: (MH⁺) m/z=363

EXAMPLE 15

2-Chloro-7-ethyl-7-hydroxy-3-methyl-9,12-dihydro-7H-cyclopenta[6,7]indolizino[1,2-b]quinoline-8,10-dione The expected product is obtained according to the process described in Example 6 (6a+6b), using the compound described in Preparation F as starting material, and replacing 2-bromo-3-bromomethylquinoline by 2-bromo-3-bromomethyl-6-chloro-7-methylquinoline.

EXAMPLE 16

(7S)-7-Ethyl-7-hydroxy-9,12-dihydro-7H-cyclopenta[6,7]indolizino-[1,2-b]quinoline-8,10-dione The expected product is obtained according to the process described in Example 1, using the compound described in Preparation I as starting material.

EXAMPLE 17

7-Ethyl-7-hydroxy-10,13-dihydrobenzo[6,7]indolizino[1,2-b]-quinolin-11(7H)-one

The expected product is obtained according to the process described in Example 1, using the compound described in Preparation J as starting material.

EXAMPLE 18

7-Ethyl-7-hydroxy-10,13-dihydrobenzo[6,7]indolizino[1,2-b]-quinoline-8,9,11(7H)-trione The expected product is obtained according to the process described in Example 1, using the compound described in Preparation K as starting material.

EXAMPLE 19

2-Ethyl-2-hydroxy-1a,10,13,13a-tetrahydro[1]benzoxireno[3',4':6,7]indolizino[1,2-b]quinolin-12(2H)-one The expected product is obtained according to the process described in Example 1, using the compound described in Preparation L as starting material.

EXAMPLE 20

7-Ethyl-7-hydroxy-7,8,10,13-tetrahydrobenzo[6,7]indolizinol[1,2-b]-quinoline-9,11-dione The expected product is obtained according to the process described in Example 1, using the compound described in Preparation 0 as starting material.

EXAMPLE 21

7-Ethyl-7-hydroxy-7,8,1 1,14-tetrahydro-12H-cyclohepta[6,7]-indolizino[11,2-b]quinolin-12-one The expected product is obtained according to the process described in Example 1, using the compound described in Preparation M as starting material.

EXAMPLE 22

7-Ethyl-7-hydroxy-11,14-dihydro-7H-cyclohepta[6,7]indolizino-[1,2-b]quinoline-9,12(8H,10H)-dione The expected product is obtained according to the process described in Example 1, using the compound described in Preparation N as starting material.

EXAMPLE 23

2,3-Difluoro-7-ethyl-7-hydroxy-10,13-dihydrobenzo[6,7]indolizino-[1,2-b]quinoline-8,11(7H,9H)-dione The expected product is obtained according to the process described in Example 1, using the compound described in Preparation G as starting material, and replacing 2-bromo-3-bromoethylquinoline by 2-bromo-3-bromomethyl-6,7-difluoroquinoline.

Mass spectrum: (MH+) m/z=383

EXAMPLE 24

7-ethyl-7-hydroxy-2,3-methylenedioxy-13-cyclobutyl-8-[2-(1,3-dioxolan)yl]-9,12-dihydro-7H-cyclopenta[6,7]indolizinol[1,2-b]quinolin-10-one The expected product is obtained according to the process described in Example 6a replacing 2-bromo-3-bromomethylquinoline by 2-bromo-3-bromomethyl-4-cyclobutyl-6,7-methylenedioxyquinoline. The latter reagent is prepared adapting the existing process known from literature [F. G. Fang et al., Tetrahedron 53 32 10953–10970 (1997)].

NMR¹H(200MHz,DMSO-d₆): δ(ppm)=0.90(3,t); 1.60–2.20 (4,m);2.40–2.70 (4,m); 2.85 (2,s), 3.80–4.10 (2,m); 5.30 (2,s); 6.25 (2,s); 7.00(1,s); 7.45 (2,s).

EXAMPLE 25

7-ethyl-7-hydroxy-2,3-methylenedioxy-13-cyclobutyl-9,12-dihydro-7H-cyclopenta[6,7]indolizino[1,2-b]quinoline-8,10-dione The expected product is obtained according to the process described in Example 6b using the compound described in Example 24 as the starting reagent.

Mass spectrum: (MH+) m/z=430

Pharmacological Study

EXAMPLE A

In vitro Activity

The murine leukaemia L1210 was used in vitro. The cells are cultured in complete RPMI 1640 culture medium containing 10% foetal calf serum, 2 mM glutamine, 50 U/ml of penicillin, 50 μg/ml of streptomycin and 10 mM Hepes, pH: 7.4. The cells are distributed on microplates and are exposed to the cytotoxic compounds for 4 doubling times, that is to say 48 hours (L1210). The number of viable cells is then quantified by a calorimetric assay, the Microculture Tetrazolium Assay (J. Carmichael et al., Cancer Res.; 47, 936-942, (1987)). The results are expressed as $IC_{50}$, which is the cytotoxic concentration that inhibits proliferation of the treated cells by 50%.

The compounds of the invention appear to be potent cytotoxic agents, the $IC_{50}$ values being markedly lower than $10^{-6}$ M.

EXAMPLE B

Pharmaceutical Composition

Formulation for the preparation of 1000 tablets containing a dose of 10 mg:

| | |
|---|---|
| Compound of Example 5 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula (I):

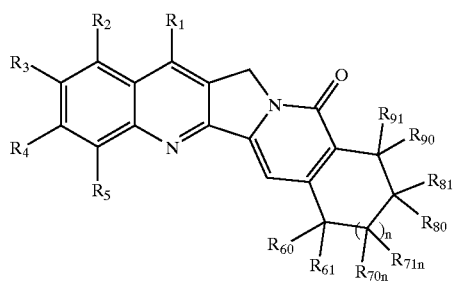

(I)

wherein:
  n is 0, 1 or 2,
  $R_1$ represents $(C_3-C_{11})$cycloalkyl or $(C_3-C_{11})$ cycloalkylalkyl,
  $R_2$, $R_3$, $R_4$ and $R_5$ are selected each independently of the others from hydrogen, halogen, alkyl, alkenyl, alkynyl, perhaloalkyl, $(C_3-C_{11})$cycloalkyl, $(C_3-C_{11})$cycloalkyl-alkyl, hydroxy, hydroxyalkyl, alkoxy, alkoxyalkyl, alkoxycarbonyl, acyloxy, carboxy, nitro, cyano, aminocarbonyl (optionally substituted on the nitrogen by one or two alkyl), and The groups $(CH_2)_p$—$NR_aR_b$ and —O—C(O)—N—$R_aR_b$, wherein p is an integer from 0 to 6, and $R_a$ and $R_b$ each independently of the other represents hydrogen, alkyl, $(C_3-C_{11})$cycloalkyl, $(C_3-C_{11})$cycloalkyl-alkyl, acyl, optionally substituted aryl or optionally substituted arylalkyl, or Ra and Rb form together with the nitrogen carrying them a pyrrolyl, piperidinyl or piperazinyl group, it being possible for each of those cyclic groups to be optionally substituted,
  or two adjacents groups $R_2$, $R_3$, $R_4$ and $R_5$ form together with the carbon atoms carrying them a group —O—$(CH_2)_t$—O, t being an integer from 1 to 3 inclusive,
  $R_{60}$, $R_{70n}$, $R_{80}$ and $R_{90}$ each independently of the others represents hydrogen, hydroxy, alkoxy, or a group O—(CO)—X or O—(CO)—NXW wherein X and W each independently of the other represents alkyl, alkenyl, alkynyl, $(C_3-C_{11})$cycloalkyl, $(C_3-C_{11})$ cycloalkyl-alkyl, optionally substituted aryl or optionally substituted arylalkyl,
  $R_{61}$, $R_{71n}$, $R_{81}$ and $R_{91}$ each independently of the others represents hydrogen, alkyl, alkenyl or alkynyl, or, taken in pairs on adjacent carbon, together form bond or oxirane, or two geminal groups ($R_{60}$ and $R_{61}$) and/or ($R_{70n}$ and $R_{71n}$) and/or ($R_{80}$ and $R_{81}$) and/or ($R_{90}$ and $R_{91}$) together form oxo or —O—$(CH_2)_{t1}$—O, $t_1$ being an integer from 1 to 3 inclusive,
  with the proviso that $R_{60}$, $R_{61}$, $R_{70n}$, $R_{71n}$, $R_{80}$, $R_{81}$, $R_{90}$ and $R_{91}$ do not all represent a hydrogen atom,
  its enantiomers, diastereoisomers, and addition salts thereof with a pharmaceutically acceptable acid or base,
  it being understood that:
    the term "alkyl" denotes a linear or branched chain having from 1 to 6 carbon atoms,
    the term "alkenyl" denotes a linear or branched chain having from 2 to 6 carbon atoms and containing from 1 to 3 double bonds,
    the term "alkynyl" denotes a linear or branched chain having from 2 to 6 carbon atoms and containing from 1 to 3 triple bonds,
    the term "alkoxy" denotes a linear or branched alkyl-oxy radical containing from 1 to 6 carbon atoms,
    the term "acyl" denotes a linear or branched alkyl-carbonyl radical containing from 1 to 6 carbon atoms,
    the term "aryl" represents phenyl or naphthyl,
    the expression "substituted" when used in relation to aryl or arylalkyl means that the groups in question are substituted by one or more halogen, and/or alkyl, alkoxy, hydroxy, cyano, nitro, and/or amino (optionally substituted by one or two alkyl),
    the expression "substituted" when used in relation to pyrrolyl, piperidinyl or piperazinyl means that the groups in question are substituted by one or more alkyl, alkoxy, aryl, arylalkyl, aryloxy and/or aryloxy-alkyl.

2. A compound of claim 1 which is 7-ethyl-7-hydroxy-2,3-methylenedioxy-13-cyclobutyl-8-[2-(1,3-dioxolan)yl]-9,12-dihydro-7H-cyclopenta[6,7]indolizino[1,2-b]quinolin-10-one.

3. A compound of claim 1 which is 7-ethyl-7-hydroxy-2,3-methylenedioxy-13-cyclobutyl-9,12-dihydro-7H-cyclopenta[6,7]indolizino[1,2-b]quinoline-8,10-dione.

4. A method for treating a living body afflicted with leukemia, colon adenocarcinoma, prostate carcinoma or lung carcinoma, comprising the step of administering to the living body an amount of a compound of claim 1 which is effective for alleviation of said condition.

5. A pharmaceutical composition useful for the treatment of leukemia, colon adenocarcinoma, prostate carcinoma or lung carcinoma, comprising as active principle an effective amount of a compound as claimed in claim 1, together with one or more pharmaceutically-acceptable excipients or vehicles.

6. A compound of claim 1 wherein $R_2$, $R_3$, $R_4$, and $R_5$ are selected from hydrogen, halogen, alkyl and alkoxy, or two of those groups, when bonded to two adjacent carbon atoms, together form methylenedioxy or ethylenedioxy, its enantiomers, diastereoisomers, and addition salts thereof with a pharmaceutically acceptable acid or base.

* * * * *

UNITED STATES PATENT AND TRADEMARK OFFICE
CERTIFICATE OF CORRECTION

PATENT NO.    : 6,699,876 B2
DATED         : March 2, 2004
INVENTOR(S)   : Gilbert Lavielle et al.

It is certified that error appears in the above-identified patent and that said Letters Patent is hereby corrected as shown below:

Title page,
Item [57], ABSTRACT,
Line 10, "$(CH_2)_P-N_aR_b$" should be -- $(CH_2)_P-NR_aR_b$ --.

Column 19,
Line 48, insert -- -8[2(1,3-dioxolan)yl] -- after "cyclobutyl".

Signed and Sealed this

Third Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,699,876 B2
DATED : March 2, 2004
INVENTOR(S) : Gilbert Lavielle et al.

It is certified that error appears in the above-identified patent and that said Letters Patent is hereby corrected as shown below:

Column 19,
Line 48, "8[2(1,3-dioxolan)yl]" (as inserted by Certificate of Correction issued August 3, 2004) should be deleted.

Signed and Sealed this

Twelfth Day of October, 2004

JON W. DUDAS
*Director of the United States Patent and Trademark Office*